United States Patent [19]

Wetterman

[11] Patent Number: 4,931,037

[45] Date of Patent: Jun. 5, 1990

[54] IN-DWELLING URETERAL STENT AND INJECTION STENT ASSEMBLY, AND METHOD OF USING SAME

[75] Inventor: Peter H. Wetterman, Pomfret, Conn.

[73] Assignee: International Medical, Inc., Danielson, Conn.

[21] Appl. No.: 257,087

[22] Filed: Oct. 13, 1988

[51] Int. Cl.⁵ .................... A61M 37/00; A61M 25/00
[52] U.S. Cl. ........................................ 604/8; 604/280
[58] Field of Search ...................... 604/8, 14, 53, 280, 604/266, 282

[56] References Cited

U.S. PATENT DOCUMENTS

| | | |
|---|---|---|
| 2,212,334 | 8/1940 | Wallerich . |
| 2,393,003 | 1/1946 | Smith . |
| 3,419,010 | 12/1968 | Williamson . |
| 3,633,585 | 1/1972 | McDonald, Jr. .................... 604/8 |
| 3,726,269 | 4/1973 | Webster, Jr. . |
| 3,890,977 | 6/1975 | Wilson . |
| 3,938,529 | 2/1976 | Gibbons . |
| 4,117,838 | 10/1978 | Hasson . |
| 4,212,304 | 7/1980 | Finney . |
| 4,307,723 | 12/1981 | Finney . |
| 4,469,483 | 9/1984 | Becker et al. . |
| 4,531,933 | 7/1985 | Norton et al. . |
| 4,568,338 | 2/1986 | Todd . |
| 4,610,657 | 9/1986 | Densow .................................. 604/8 |
| 4,643,716 | 2/1987 | Drach . |
| 4,671,795 | 6/1987 | Mulchin . |
| 4,713,049 | 12/1987 | Carter .................................... 604/8 |
| 4,790,809 | 12/1988 | Kuntz .................................... 604/8 |
| 4,790,810 | 12/1988 | Pugh, Jr. et al. ...................... 604/8 |

Primary Examiner—Robert A. Hafer
Assistant Examiner—Kerry Owens

[57] ABSTRACT

A stent has a first tubular portion with a straight section and a curled section at the proximal end thereof, a second tubular portion curl providing a curled section at the distal end. The second portion has a larger diameter than the first portion and receives the straight section therein which is bonded thereon. The end of the straight section within the second portion forms a shoulder for abutment by an injection catheter to inject the stent into a patient. The outer surface of the distal portion is relatively soft to avoid bladder irritation.

17 Claims, 2 Drawing Sheets

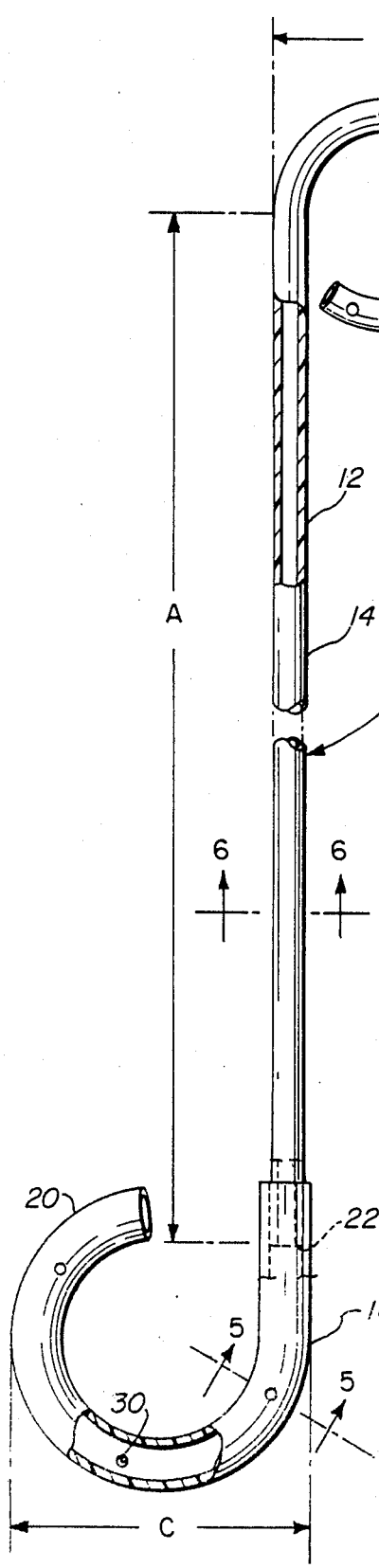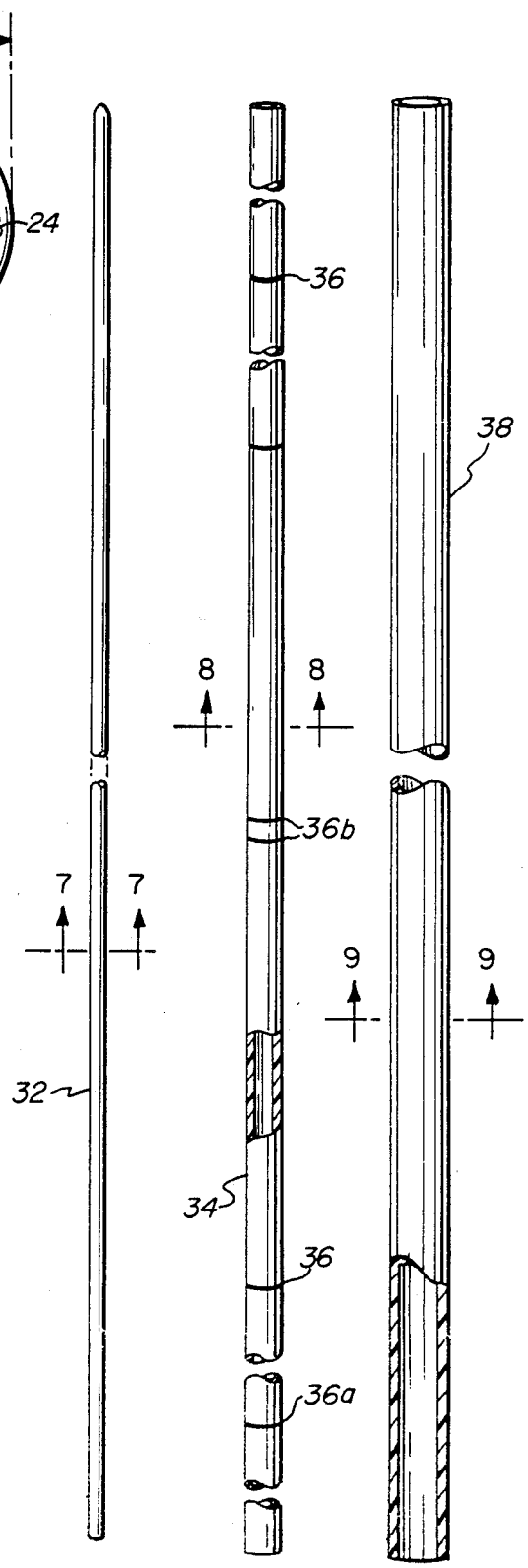
FIG. 1  FIG.2  FIG.3  FIG.4

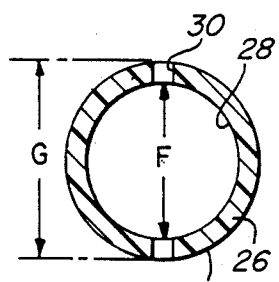
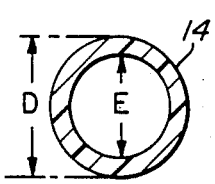
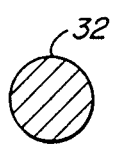
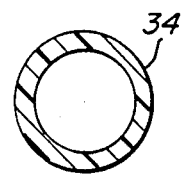
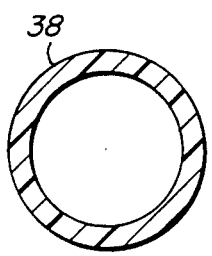
FIG. 5  FIG. 6  FIG. 7  FIG. 8  FIG. 9
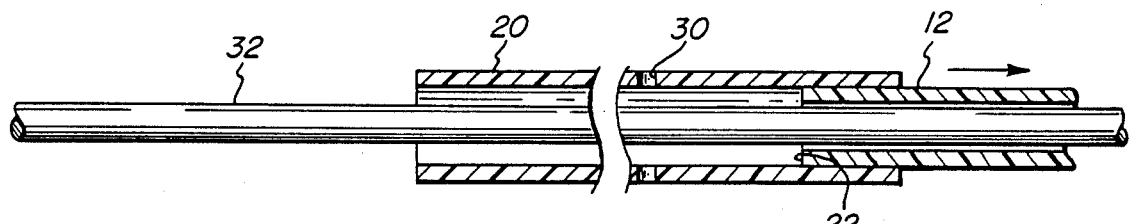
FIG. 10
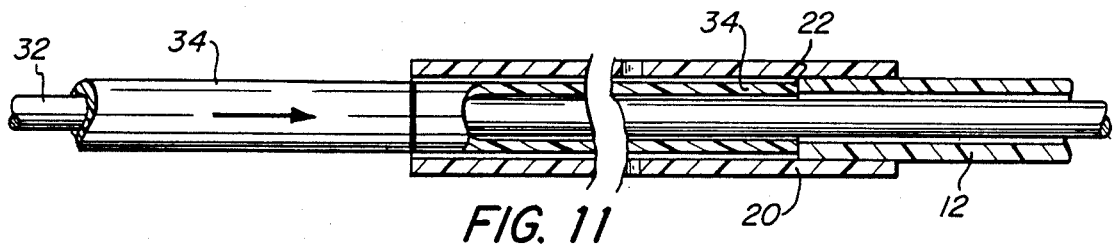
FIG. 11
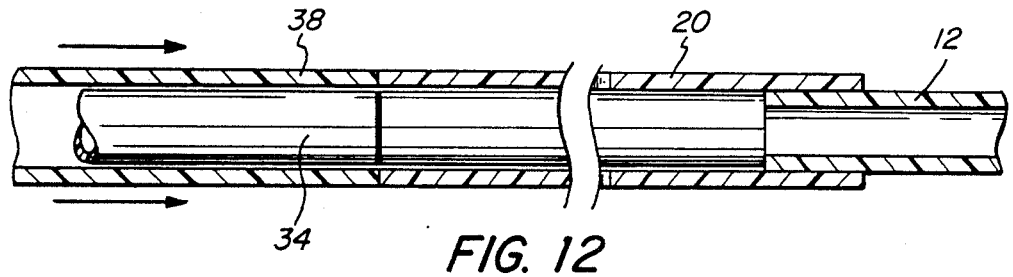
FIG. 12

IN-DWELLING URETERAL STENT AND INJECTION STENT ASSEMBLY, AND METHOD OF USING SAME

BACKGROUND OF THE INVENTION

The present invention relates to in-dwelling ureteral catheter stents and to the method of using the same.

In-dwelling ureteral catheter stents or drainage tubes have been used to bypass ureteral obstructions or uretero-vaginal fistulas and maintain urinary drainage. Stents made of straight lengths of open-ended tubing are widely used for this purpose and have provided drainage for sustained periods of time. However, the use of such open-ended tubing has not been completely satisfactory in that, in some instances, the tubing has migrated, and, in other cases, it has been expelled.

To combat the problem of migration or expulsion, stents have been designed which are closed at the proximal end to facilitate passage into the ureter, and which have a flange or other formation at the distal end to preclude upward migration of the stent. U.S. Pat. Nos. 4,212,304 and 4,307,723 disclose ureteral stents with ends having portions with hooks or curls which have been effective in preventing migration and expulsion. Such stents can be introduced both endoscopically and during open surgery.

Other stents having formed proximal and distal ends to combat migration and expulsion are disclosed in U.S. Pat. Nos. 4,643,716; 4,610,657; and 4,713,049.

At the present time, there are two general types of ureteral stents available. One type is made of a soft material, and the other is made of a stiff material. Each requires a different method of placement within the ureter and each has its advantages and disadvantages. A ureteral stent made from a soft material has a closed proximal tip which is inserted into the kidney. This type of stent is placed in the ureter by inserting a stiff stylet through the distal end until it abuts against the proximal tip. The stent stiffened by the stylet is guided into the bladder with the use of a standard cystoscope. Once the ureteral orifice is located, the stent is advanced up the ureter by pushing the stylet against the closed proximal end.

The disadvantage of using a stent of soft material is that it must be stiffened and guided by a stylet. This increases the possibility for the stent to migrate and perforate the ureteral wall, especially if the ureter is partially obstructed or tortuous. After placement, soft stents have a greater tendency to migrate distally and proximally because soft curls formed therein will straighten easily.

A ureteral stent made from a stiff material has open distal and proximal ends. The stent is inserted by first inserting the guide wire through the ureter into the kidney and the stent is fed over the guide wire which straightens its curls as it travels thereover. A push rod is slid over the guide wire until it abuts the distal end of the stent. Because the material is stiff, this stent may be advanced along the guide wire with the push rod without collapsing the stent and with less chance of perforating the ureteral wall. Once the stent is in place, both the push rod and guide wire are removed and the distal and proximal ends curl to prevent the stent from migrating or being expelled. The major disadvantage of using the stiff material stent is patient discomfort, because the distal curl tends to irritate the bladder wall when the bladder is empty.

With the development of the extracorporeal shockwave lithotriptor (ESWL) which provides a non-invasive method of breaking kidney stones using shock waves, the use of stents has greatly increased, and most patients with large kidney stones are stented prior to ESWL procedures. This is to aid in the migration of sediment from the kidney to the bladder as well as to prevent the possible formation of steinstrasse (stone street) which occur when a large fragment of the disintegrated stone blocks the ureter. By stenting a patient prior to ESWL, large fragments cannot enter the ureter and cause urinary blockage.

It is an object of the present invention to provide a new and improved in-dwelling ureteral stent with curled end portions for anchoring the stent in the kidney and bladder.

It is also an object to provide such a stent which affords greater comfort to the patient.

Another object is to provide a catheter assembly permitting facile and accurate placement of the stent and facilitating irrigation of the kidney.

A further objection is to provide an improved method for placement of a ureteral stent and irrigating the kidney.

SUMMARY OF THE INVENTION

It has now been found that the foregoing and related objects may be readily attained in an in-dwelling ureteral stent comprising a first flexible tubular portion with a straight section and a curled section at the proximal end, and a second flexible portion providing a tubular curled section at the distal end. The second portion has a larger diameter than the outer diameter of the first portion and seats therein the end of the straight section of the first portion which is bonded thereto. The end of the straight section within the second portion forms a shoulder against which an injection push catheter may abut. Both portions of the stent are fabricated from synthetic resin, and the second portion has a surface which is softer than that of the first portion.

In the preferred embodiments, the tubular portions are radio-opaque and the second portion is formed of two layers of differing durometer resin, the outer layer being softer than the inner. The curled sections of the first and second portions have drainage holes therein.

The stent is used in an injection push ureteral catheter assembly which additionally includes a guide wire of a lesser diameter extending in the passage through the stent and having a stiffness sufficient to straighten the curled portions thereof. Also included is a tubular push catheter having a passage therethrough in which is received the guide wire. The wall of the push catheter has a diameter so that it seats within the passage of the second portion of the stent and abuts the shoulder to permit the stent to be pushed along the guide wire as the push catheter is pushed therealong. Desirably, the push catheter has markings along its length adjacent the end external to the stent.

Preferably, the assembly also includes a tubular stent positioner with a passage slidably seating the push catheter therein and the end of the stent positioner abuts the distal end of the wall of the second portion of the stent. The push catheter and stent positioner are fabricated from synthetic resin.

In the method of inserting the ureteral stent into the ureter of a patient, the guide wire is inserted through the ureter and into the kidney of the patient. The ureteral stent is then slid onto the guide wire, the curled sections being straightened by the guide wire as they pass thereonto. A tubular push catheter has a passage therethrough and is slid onto the guide wire with its proximal end being seated within the passage of the second portion of the stent and abutting the shoulder. The push catheter is pushed, and it and the stent slide along the guide wire until the proximal end of the stent is disposed within the renal pelvis. After the guide wire is removed from the stent and the push catheter, the proximal end of the stent curls within the renal pelvis to anchor it therein. The push catheter is withdrawn from the passage in the second portion of the stent, and the second portion then curls in the patient's bladder.

Moreover, the method of use may include the additional steps of sliding a tubular stent positioner over the push catheter and against the distal end of the second portion of the stent prior to withdrawal of the push catheter from the stent. A Luhr connector may be attached to the stent positioner, and the kidney may be irrigaged through the stent and the push catheter.

In the normal method of use, the stent positioner is partially withdrawn until a marking on the push catheter external to the stent is seen, and then both the push catheter and stent positioner are removed.

BRIEF DESCRIPTION OF THE DRAWINGS

FIG. 1 is a fragmentary view of a ureteral stent embodying the invention with portions of the wall broken away;

FIG. 2 is a fragmentary view of a guide wire used in connection therewith;

FIG. 3 is a fragmentary view of an injection or push catheter with a portion of the wall broken away;

FIG. 4 is a fragmentary view of a stent positioner with a portion of the wall broken away;

FIG. 5 is a sectional view of the stent along the line 5—5 of FIG. 1 and drawn to an enlarged scale;

FIG. 6 is a sectional view of the stent along the line 6—6 of FIG. 1 and drawn to an enlarged scale;

FIG. 7 is a sectional view of the guide wire along the line 7—7 of FIG. 2 and drawn to an enlarged scale;

FIG. 8 is a sectional view of the push catheter along the line 8—8 of FIG. 3 and drawn to an enlarged scale;

FIG. 9 is a sectional view of the stent positioner along the line 9—9 of FIG. 4 and drawn to an enlarged scale;

FIG. 10 is a fragmentary sectional view of the distal end of the stent seated on the guide wire with the distal curl straightened in the initial stage of the injection process;

FIG. 11 is a similar view showing the push catheter disposed on the guide wire and abutting the shoulder of the stent to push it along the guide wire; and FIG. 12 is a similar view showing the stent positioner disposed on the push catheter and abutting the distal end of the stent.

DETAILED DESCRIPTION OF PREFERRED EMBODIMENT OF THE INVENTION

A stent embodying the present invention is shown in FIG. 1 and is generally designated by the numeral 10; it has a first tubular portion 12 with an elongated straight section 14 and a curled section 16 at the proximal end. The stent 10 also has a second tubular portion 18 of greater diameter than the first tubular portion 12 and it provides a curled section 20 at the distal end. The larger diameter tubular second portion 18 receives the end of the smaller diameter straight section 14 of the first tubular portion 12, and the end of the tubular portion 12 thus defines an internal shoulder 22 within the passage of the second tubular portion 18.

As used herein, "proximal end" refers to the end of the stent which will be disposed within the kidney or renal pelvis, and "distal end" refers to the end which will be disposed within the bladder.

To provide sufficient rigidity to prevent collapsing of the wall, the first tubular portion 12 is fabricated from a synthetic resin having a durometer of about 40 on the Shore "D" scale, and the resin contains 20% by weight barium sulfate to make it radio-opaque, thus facilitating facilitate positioning by means of a fluoroscope or like apparatus. A series of three axially spaced (one centimeter apart) drain openings 24 is provided in the curled section 16 along both sides thereof.

As seen in FIG. 5, the second tubular portion 18 is formed from two layers of synthetic resin, the outer layer 26 being fabricated from a softer resin than the resin of the tubular portion 12 and that of the inner layer 26 which may have the same durometer as that of the tubular portion 12. In practice, a desirable stent utilizes for the outer layer a resin having a durometer of approximately 75 on the Shore A scale and, for the thin inner layer, a resin having a durometer of about 70 on the Shore D scale. This composite structure allows the lower curled section 20 to be relatively soft to minimize irritation of the bladder wall while the relatively stiff inner layer prevent the internal surfaces from sticking to each other. A series of three drain holes is spaced one centimeter apart along both sides of the curled section 20.

As seen in FIG. 1, the curled section 16 curls in a direction opposite to the direction of the curl in the curled section 20. To firmly assemble the two portions 12,18, sonic welding or an adhesive is utilized to bond the outer surface of the tubular portion 12 to the inner surface of the tubular portion 18.

The guide wire 16 is relatively stiff so that it will cause the curled sections 16,20 to straighten as they pass thereover. To facilitate movement of the stent 10 thereover, it is desirably coated with a resin providing low friction characteristics such as polytetrafluoroethylene. The diameter of the guide wire 32 is slightly less than the inner diameter of the tubular portion 12 so that it will provide good guidance therefor.

The push catheter seen in FIG. 3 is also fabricated from synthetic resin as a tubular member with inner and outer diameters approximating those of the first tubular portion 12. Spaced along its length are a series of markings 36 for a purpose to be described more fully hereinafter.

In FIG. 4, the stent positioner is seen to be a tubular member of synthetic resin, and it has inner and outer diameters corresponding to those of the second tubular portion 18.

In use of the catheter assembly of the present invention, a cystoscope is conveniently employed during placement. The guide wire is first introduced into the ureter and guided therealong until the proximal end rests in the renal pelvis. Thereafter, the proximal end of the stent 10 is placed upon the exposed end of the guide wire 32 and the stent is slid therealong with the curled sections 16,20 being straightened thereby. The push catheter 34 is then slid onto the guide wire 32 and its proximal end seats in the second tubular portion 18 of the stent 10 in abutment against the shoulder 22.

Using the push catheter 34, the stent 10 is advanced along the guide wire 32 until the distal end of the stent 10 is at the uretero-vesical junction. Then, while holding the stent 10 in place with the push catheter 34, the guide wire 32 is pulled out by an assistant. When the guide wire 32 is removed, the curled section 16 at the proximal end of the stent 10 will form its curl 12 in the renal pelvis.

Next, the cystoscope is removed, leaving the push catheter 34 in place inside the second portion 18 of the stent 10. Since the push catheter 34 is within the straightened curled section 20, it prevents the curl from forming. Next, the stent positioner 38 of FIG. 4 is slid over the push catheter 34 until it abuts the distal end of the second portion 18 as shown in FIG. 12. Proper placement of the stent is verified with fluoroscopy or standard radiography.

When injection of a contrast media is necessary or anticipated, a Luer injection port (not shown) is placed on the injection catheter and tightened. The end cap of the Luer injection port is removed and a syringe (not shown) containing the contrast media is connected thereto and the contrast media is injected through the push catheter 34 and stent 10.

After the stent 10 is placed and/or no further injection procedure is necessary, the push catheter 34 is ready to be removed. The stent positioner 38 is slid over the push catheter 34, passing it into the bladder until only the outermost single black band 36a on the push catheter 34 is visible. This indicates that the stent positioner is abutting the distal end of the stent 10.

Holding the stent positioner 38 firmly in place, the push catheter 34 is slowly pulled out of the stent positioner 38 until the double black band 36b becomes visible. This indicates that the push catheter 34 is disengaged from the distal end of the stent 10. Then the stent positioner 38 and the push catheter 34 are removed from the patient.

As the push catheter 34 is removed from the straightened curled section 20, the memory of the curled section 20 causes it to return to the curled position seen in FIG. 1 and thus lock the distal end of the stent 10 in the bladder to prevent migration of the stent through the ureter into the kidney. The softer material of the curled section 20 minimizes irritation and damage to the bladder.

Stents embodying the invention may desirably have the following dimensions and characteristics:

| | |
|---|---|
| Guide wire 32: | .038" O.D., Teflon coated, 150 cm long |
| Stent First Tubular Portion 12: | 5 French O.D., .041 inch I.D., 70 Shore "D" polyurethane, length 22–30 cm in two centimeter increments (not including curl) |
| Stent Second Tubular Portion 18: | .101 inch O.D., .071 inch I.D., outer layer 75 Shore "A":, inner layer 70 Shore "D" |
| Push Catheter 34: | Diameters same as stent 10 in diameter; 26 inches long |
| Stent Positioner 38: | Diameters same as stent second tubular portion; 13 inches long |

Because the optimum stent will vary with the ureteral and renal dimensions of the patent, different sizes are desirable. The following table sets forth dimensions for various sizes of stents using the dimensional reference designations in FIGS. 1–5:

| Stent Size | Centimeters A | Inches B | C | D | E | F | G |
|---|---|---|---|---|---|---|---|
| 4.8 Fr. | 22,24,26,28,30 | .700 | .900 | .063 | .041 | .066 | .109 |
| 6.0 Fr. | 22,24,26,28,30 | .700 | .900 | .079 | .045 | .082 | .112 |
| 7.0 Fr. | 22,24,26,28,30 | .700 | .900 | .092 | .052 | .095 | .135 |
| 8.0 Fr. | 22,24,26,28,30 | .700 | .900 | .105 | .065 | .018 | .148 |

While the proximal and distal ends of the stent have been described as curled sections, other functionally equivalent shapes may be used to prevent migration or expulsion, such as pig-tails and spring shapes so long as they may be straightened on the guide wire. Although the preferred resins are polyurethanes, various other resins may also be employed.

Thus, it may be seen that the objects of the invention set forth, as well as those made apparent from the foregoing description, are efficiently attained. Although a preferred embodiment of the invention has been set forth for purposes of disclosure, modifications to the disclosed embodiment of the invention, as well as other embodiments thereof, may occur to those skilled in the art. Accordingly, the appended claims are intended to cover all embodiments of the invention and modifications to the disclosed embodiments which do not depart from the spirit and scope of the invention.

I claim:

1. An in-dwelling ureteral stent comprising:
   (a) a first flexible tubular portion with a straight section and a curled section at the proximal end thereof; and
   (b) a second flexible portion providing a tubular curled section at the distal end, said second portion having a larger inner diameter than the outer diameter of said first portion and seating therein the end of said straight section of said first portion, said seated end being bonded to the inner surface of said second portion, whereby the end of said straight section within said section portion forms an internal shoulder facing said distal end within said second portion and against which an injection push catheter may abut, said stent being fabricated from synthetic resin and said second portion having an outer surface which is softer than the outer surface of said first portion.

2. The stent of claim 1 wherein said tubular portions are radio-opaque.

3. The stent of claim 1 wherein said second portion is formed of two layers of differing durometer resin, the outer layer being softer than the inner.

4. The stent of claim 1 wherein said curled sections of said first and second portions have drainage holes therein.

5. An injection push ureteral catheter assembly comprising:
   (a) an in-dwelling ureteral stent comprising a first flexible tubular portion with a straight section and a curlable section at the proximal end thereof and a second flexible portion providing a tubular curlable section at the distal end, said second portion having a larger inner diameter than the outer diameter of said first portion and seating therein the end of said straight portion of said first portion, said seated end being bonded to the inner surface of said second portion, whereby the end of said straight section within said second portion forms an internal shoulder facing said distal end within said second portion and against which an injection push catheter may abut, said stent being fabricated from synthetic resin and said second portion having an outer surface which is softer than the outer surface of said first portion;

(b) a guide wire of a lesser diameter extending in the passage through said stent and having a stiffness sufficient to straighten said curled portions thereof; and (c) a tubular push catheter having a passage therethrough in which is received said guide wire, the wall of said push catheter having a diameter smaller than the inner diameter of said second portion and seating within the passage of said second portion of said stent, and said push catheter being of larger diameter than the inner diameter of said first portion, said inner end of push catheter abutting said internal shoulder to permit said stent to be pushed along said guide wire as said push catheter is pushed therealong.

6. The catheter assembly of claim 5 wherein said push catheter has markings along its length adjacent the end external to said stent.

7. The catheter assembly of claim 5 wherein said tubular portions are radio-opaque.

8. The catheter assembly of claim 5 wherein said second portion is formed of two layers of differing durometer resin, the outer layer being softer than the inner.

9. The catheter assembly claim 5 wherein said curled sections of said first and second portions have drainage holes therein.

10. The catheter assembly of claim 6 wherein said assembly includes a tubular stent positioner with its passage being of larger inner diameter than the outer diameter of said push catheter and slidably seating said push catheter therein, the end of said stent positioner abutting the distal end of the wall of said second portion of said stent.

11. The catheter assembly of claim 10 wherein said push catheter and stent positioner are fabricated from synthetic resin.

12. In the method of inserting a ureteral stent into the ureter of a patient, the steps comprising:

(a) inserting a guide wire through the ureter and into the kidney of the patient;

(b) sliding onto said guide wire a ureteral stent comprising a first flexible tubular portion with a straight section and a curled section at the proximal end thereof and a second flexible portion providing a tubular curled section at the distal end, said second portion having a larger inner diameter than the outer diameter of said first portion and seating therein the end of said straight section of said first portion, said seated end being bounded to the inner surface of said second portion, whereby the end of said straight section within said second portion forms an internal shoulder facing said distal end within said second portion and against which an injection push catheter may abut, said stent being fabricated from synthetic resin and said second portion having an outer surface which is softer than the outer surface of said first portion, said curled sections being straightened by said guide wire as they pass thereonto;

(c) sliding onto said guide wire a tubular push catheter having a passage therethrough receiving said guide wire, the wall of said push catheter having an outer diameter smaller than the inner diameter of said second portion and larger than the inner diameter of said first portion, said push catheter having its proximal end seated within said passage of said second portion of said stent and abutting said internal shoulder;

(d) continuing to push said push catheter, and thereby said stent, along said guide wire until the proximal end of said stent is disposed within the renal pelvis;

(e) removing said guide wire from said stent and said push catheter whereby the proximal end of said stent curls within said renal pelvis to anchor it therein; and (f) withdrawing said push catheter from said passage in said second portion of said stent whereby said second portion curls in the patient's bladder.

13. In the method of claim 12, the additional step of sliding a tubular stent positioner over said push catheter and against the distal end of said second portion of said stent prior to withdrawal of said push catheter from said stent.

14. In the method of claim 13, the additional step of partially withdrawing the stent positioner until a marking on said push catheter external to said stent is seen, and then removing both said push catheter and stent positioner.

15. The method of claim 12 wherein said tubular portions of said stent are radio-opaque.

16. The method of claim 12 wherein said second portion is formed of two layers of differing durometer resin, the outer layer being softer than the inner.

17. The method of claim 12 wherein said curled sections of said first and second portions have drainage holes therein.

* * * * *